United States Patent [19]

Shudo

[11] Patent Number: 5,420,145
[45] Date of Patent: May 30, 1995

[54] CARBOXYLIC ACID DERIVATIVE

[75] Inventor: Koichi Shudo, Accomodations for Officials, 2-25-6-102, Higashiyama, Megura-ku, Tokyo, Japan

[73] Assignees: Koichi Shudo; Shionogi Pharmaceutical Co., Ltd., both of Japan

[21] Appl. No.: 35,612

[22] Filed: Mar. 23, 1993

[51] Int. Cl.$^6$ .................... A61K 31/44; A61K 31/445; C07D 213/40; C07D 213/46
[52] U.S. Cl. .................... 514/352; 514/354; 514/355; 514/356; 514/357; 546/309; 546/310; 546/337; 546/323; 546/322
[58] Field of Search ............... 514/354, 355, 356, 357, 514/352, 648, 649; 546/375, 310, 337, 309, 322; 564/342

[56] References Cited

FOREIGN PATENT DOCUMENTS 93906086 4/1993 WIPO .

OTHER PUBLICATIONS

Warrell et al "Acute Promyelocytic Leukemia" New Eng J Med 329 177–189 (1993).
Tucker et al. "Novel Inhibitors of Proly 4–Hydroxylase" J. Med Chem. 35 804–807 (1992).
Kateka et al. CA86: 25276 (1976).
Ismael et al CA68: 29670h (1967).
Albuquerque CA117: 40006x (1993).
Tucker CA116: 123761 (1992).
Northfleet CA111: 209k (1988).
Bacha CA109: 16611e (1987).
Rahalkav CA106: 196222y (1986).
Cahn CA77: 164257e (1972).
Ueda CA109: 185398w (1988).
Bouley CA102: 148872f (1984) CA102: 113058t (1984).
Spauo CA77: 43074j (1972).
Orzalesi CA67: 108615b (1967).
"The Retinoids and Human Cancer", Chapter 15, pp. 618–619 (1994).

Primary Examiner—Celia Chang
Attorney, Agent, or Firm—Cushman Darby & Cushman

[57] ABSTRACT

Carboxylic acid derivatives having potent retinoid-type pharmacological activities are disclosed. The compounds disclosed are represented by the following formula:

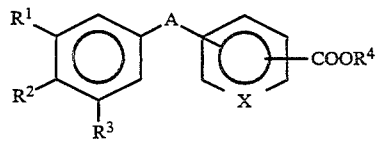

wherein $R^1$, $R^2$, and $R^3$ independently represent a hydrogen atom or an alkyl group with the exception that all of $R^1$, $R^2$, and $R^3$ do not simultaneously represent hydrogen atoms and $R^1$ together with $R^2$ optionally represent a cyclic structure formed by the combination thereof; $R^4$ represents a hydrogen atom or an alkyl group; X represents a nitrogen atom or C—OH; and A represents —CO—NH— or —NH—CO—.

4 Claims, No Drawings

CARBOXYLIC ACID DERIVATIVE

BACKGROUND OF THE INVENTION

FIELD OF THE INVENTION

The present invention relates to carboxylic acid derivatives. More specifically, the present invention relates to carboxylic acid derivatives having retinoic acid type pharmacological activities.

Retinoic acid (Vitamin A acid) is considered to be an active metabolite of Vitamin A. This compound has extremely important pharmacological activity for the maintenance of life. For instance, it induces differentiation on embryonic immature cells by which mature cells having characterized functions are produced. It also accelerates the proliferation of cells. From a clinical standpoint, retinoic acid is found to be useful for the treatment of avitaminosis of Vitamin A, epithelial hyperkeratosis, leukemia, and certain types of cancer. Various derivatives of Vitamin A prepared to date, such as the benzoic acid derivatives disclosed in Japanese Patent Unexamined Publication Nos. 61-22047 and 61-76440, are found to have such pharmcological activities. These compounds, including retinoic acid, which exhibit retinoic acid-type pharmacological activities are referred to as retinoids. However, all of the presently known retinoids are benzoic acid-type derivatives like those disclosed in the aforementioned publications, and no pyridine carboxylic acid-type retinoid is known to date.

SUMMARY OR THE INVENTION

The inventor of the present invention has conducted research toward the development of useful retinoids, and as a result, found that carboxylic acid derivatives represented by the following formula:

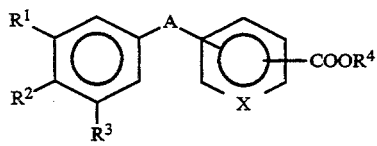

have extremely high retinoic acid-type pharmacological activities. The present invention was achieved on the basis of these findings.

The present invention thus provides a carboxylic acid derivative having the above-described formula wherein $R^1$, $R^2$, and $R^3$ independently represent a hydrogen atom or an alkyl group with the exception that all of $R^1$, $R^2$, and $R^3$ do not simultaneously represent hydrogen atoms and $R^1$ together with $R^2$ optionally represent a cyclic structure formed by the combination thereof; $R^4$ represents a hydrogen atom or an alkyl group; X represents a nitrogen atom or C—OH; and A represents —CO—NH— or —NH—CO—.

In accordance with another embodiment of the present invention, there is provided a pharmaceutical composition comprising an effective amount of at least one of the above-described described carboxylic acid derivatives or their pharmaceuticaloly acceptable salts together with a pharmaceutically acceptable carrier or coating.

In accordance with yet another embodiment of the present invention, there are also provided methods for treating avitaminosis of Vitamin A, epithelial hyperkeratosis, and leukemia comprising the step of administering an effective amount of the carboxylic acid derivative described above to a patient.

Further objects, features and advantages of the present invention will become apparent from the Detailed Explanation of the Preferred Embodiments which follows, when read in light of the accompanying Examples.

DETAILED EXPLANATION OF THE PREFERRED EMBODIMENTS

In the above formula, $R^1$, $R^2$, and $R^3$ independently represent a hydrogen atom or an alkyl group. The alkyl group may be a straight- or branched-chain alkyl having 1 to 12 carbon atoms, preferably 2 to 8 carbon atoms, and most preferably 2 to 6 carbon atoms. More specifically, examples of the alkyl include methyl, ethyl, propyl, isopropyl, n-butyl, sec-butyl, tert-butyl, adamantyl, and the like. Among these substituents, $R^1$, $R^2$, and $R^3$ do not simultaneously represent hydrogen atoms, and where any two substituents or all of these substituents are alkyl groups, each alkyl group may be different from the others. $R^1$ together with $R^2$ may optionally represent a cyclic structure formed by the combination thereof, which may further be substituted with one or more alkyl groups. Where cyclic structures are formed, the ring formed may be a 5 to 7 membered-ring, preferably a 6-membered ring, and the alkyl group substituted on the ring is preferably a methyl group. One specific example where such cyclic structures are formed is 5,6,7,8-tetrahydro-5,5,8,8-tetramethyl-2-naphthalenyl group formed with these substituents and phenyl nucleus.

$R^4$ represents a hydrogen atom or an alkyl group. The alkyl group may be an alkyl having 1 to 6 carbon atoms, preferably 1 to 4 carbon atoms. Specific examples of the alkyl group include, for example, methyl, ethyl, propyl, isopropyl, n-butyl, sec-butyl, and tert-butyl. Most preferably, methyl or ethyl group is used.

In the above-described general formula, X represents a nitrogen atom or C—OH, and A represents —CO—NH— or —NH—CO—. The ring including X forms an aromatic ring. Each of the substituent A and the substituent —$CO_2R_4$ may be substituted on the aromatic ring at any of the positions of ortho, meta, or para with reference to X. For example, where X is a nitrogen atom and A represents —NH—CO—, the aromatic ring formed may be, for example, 5-carbamoylpyridine-2-carboxylic acid and esters thereof, or 6-carbamoylpyridine-3-carboxylic acid and esters thereof. Where X is C—OH and A represents —NH—CO—, the aromatic ring formed may be, for example, 3-hydroxy-4-carbamoyl-benzoic acid or esters thereof. Where X is C—OH and A represents —CO—NH—, the aromatic ring formed may be, for example, 3-hydroxy-4-carboxamide-benzoic acid or esters thereof.

Examples of the compound of the present invention include, for example:

5(5,6,7,8-tetrahydro-8,8-dimethyl-2-naphthalenylcarbamoyl)pyridine-carboxylic acid;

5(5,6,7,8-tetrahydro-5,5,8-trimethyl-2-naphthalenylcarbamoyl) pyridine-2-carboxylic acid;

5-(5,6,7,8-tetrahydro-5,5,8,8-tetramethyl-2-naphthalenylcarbamoyl) pyridine-2-carboxylic acid;

5-(5,6,7,8-tetrahydro-5,5,8,8-tetramethyl-2-naphthalenylcarboxamido) pyridine-2-carboxylic acid;

methyl 5-(5,6,7,8-tetrahydro-5,5,8,8-tetramethyl-2-naphthalenyl-carbamoyl)pyridine-2-carboxylate;

5-(5,6,7,8-tetrahydro-5,5,8,8-tetramethyl-4-methyl-2-naphthalenylcarbamoyl)pyridine-2-carboxylic acid;
6-(5,6,7,8-tetrahydro-5,8-dimethyl-2-naphthalenylcarbamoyl)pyridine3-carboxylic acid;
6-(5,6,7,8-tetrahydro-5,5,8,8-tetramethyl-2-naphthalenylcarbamoyl) pyridine-3-carboxylic acid;
methyl 6-(5,6,7,8-tetrahydro-5,5,8,8-tetramethyl-2-naphthalenyl-carbamoyl)pyridine-3-carboxylate;
6-(5,6,7,8-tetrahydro-5,5,8,8-tetramethyl-2-naphthalenylcarboxamido) pyridine-3-carboxylic acid;
methyl 6-(5,6,7,8-tetrahydro-5,5,8,8-tetramethyl-2-naphthalenyl-carboxamido)pyridine-3-carboxylate;
6-(3,4-diisopropylphenylcarbamoyl)pyridine-3-carboxylic acid;
5-(3,4-diisopropylphenylcarbamoyl)pyridine-2-carboxylic acid;
6-(3,5-di-tert-butylphenylcarbamoyl)pyridine-3-carboxylic acid;
3-hydroxy-4-(5,6,7,8-tetrahydro-8,8-dimethyl-2-naphthalenyl-carbamoyl)benzoic acid;
3-hydroxy-4-(5,6,7,8-tetrahydro-5,5,8,8-tetramethyl-2-naphthalenylcarbamoyl)benzoic acid;
3-hydroxy-4-(5,6,7,8-tetrahydro-5,5,8,8-tetramethyl-2-naphthalenylcarboxamide)benzoic acid;
methyl 3-hydroxy-4-(5,6,7,8-tetrahydro-5,5,8,8-tetramethyl-2-naphthalenylcarboxamide)benzoate; and
methyl 3-hydroxy-4-(5,6,7,8-tetrahydro-5,5,8,8-tetramethyl-2-naphthalenylcarbamoyl)benzoate. However, the present invention is not limited to these exemplified compounds.

The compounds of the present invention represented by the above formula may be converted to alkali addition salt, preferably pharmacologically acceptable alkali addition salt. The pharmacologically acceptable salts of the compounds of the present invention may be inorganic salts such as, for example, sodium, potassium, and calcium salt, and organic alkali salts such as, for example, ammonium salts, methylamine, ethylamine, dimethylamine, triethylamine, ethanolamine, piperidine, and piperazine salts.

The carboxylic acid derivatives of the present invention can be prepared by various processes such as, for example, a process comprising the steps of treating a monoester of a pyridine carboxylic acid with thionyl chloride, treating the result with an aniline derivative or a tetrahydronaphthylamine derivative, and then optionally hydrolyzing the resulting ester; or a process comprising the steps of treating a monoester of a hydroxybenzene dicarboxylic acid such as hydroxyphthalic acid, hydroxyisophthalic acid, or hydroxyterephthalic acid, treating the result with an aniline derivative or a tetrahydronaphthylamine derivative, and then optionally hydrolyzing the result. In these processes, 3,4-diisopropylaniline, 3,5-di-tert-butylaniline, or 3-tert-butylaniline is preferably used as the aniline derivative, and 5,6,7,8-tetrahydro-5,5,8,8-tetramethyl-2-naphthylamine is prefeably used as the tetrahydronaphthylamine derivative. Where the carboxamide derivatives are prepared, an aminopyridine carboxylic acid, an ester of aminohydroxybenzoic acid or the like may be treated with an acid chloride. As the acid chloride, diisopropylbenzoic acid chloride or 5,6,7,8-tetrahydro-5,5,8,8-tetramethyl-2-naphthalenecarboxylic acid chloride may be used.

The carboxylic acid derivatives of the present invention have retinoic acid-type pharmacological activities and are useful for the treatment of diseases such as, for example, avitaminosis of Vitamin A, epithelial hyperkeratosis, leukemia, cancer, or immunological diseases.

The carboxylic acid derivatives of the present invention and their Pharmacologically acceptable salts may be administered orally or parenterally to a patient preferably as a pharmaceutical composition comprising an effective amount of at least one of the compounds of the present invention or their salts together with a pharmaceutically acceptable carrier or coating. The pharmaceutical composition suitable for oral administration may be, for example, tablet, capsule, powder, subtilized granule, granule, solution, or syrup. The pharmaceutical composition suitable for parenteral administration may be injection, suppository, inhalant, eye drop, nasal drop, ointment, or cataplasm. Any ordinarily used pharmaceutically acceptable carrier or coating can be used for the preparation of the pharmaceutical composition. For example, excipient, disintegrant or agent for accelerating disintegration, binder, lubricant, coating agent, pigment, diluent, base, solubilizing agent or solubilizer, isotonicity, pH adjusting agent, stabilizer, propellant, and adhesive may be-used as such carriers or coatings.

The dose of the pharmaceutical composition of the present invention for an adult patient may generally be from about 0.01 mg/kg to 30 mg/kg per day for oral administration, which may be increased or decreased depending on the age or conditions of the patient being treated.

EXAMPLES

The present invention will be hereinafter explained more specifically by way of examples. However, the present invention is not be limited to these examples.

Example 1

5-(5,6,7,8-Tetrahydro-5,5,8,8-tetramethyl-2-naphthalenyl-carbamoyl)pyridine-2-carboxylic acid Pyridine-2,5-dicarboxylic acid 2-monomethyl ester (139 mg) was dissolved in 5 ml of dry benzene and the solution was refluxed for 1 hour after 1 ml of thionyl chloride was added. The solvent and excess thionyl chloride were removed by evaporation under a reduced pressure, and then the residue was dried. The residue was dissolved in newly added benzene (5 ml), and the solution was left to stand overnight after 5,6,7,8-tetrahydro-5,5,8,8-tetramethyl-2-naphthylamine (156 mg) was dissolved in the mixture of 5 ml benzene and 1 ml pyridine was added. The reaction mixture was added with water and extracted with ethyl acetate. The extract was washed with water and dried, and then the solvent was removed to give methyl 5(5,6,7,8-tetrahydro-5,5,8,8-tetramethyl-2-naphthalenylcarbamoyl) pyridine-2-carboxylate (218 mg, yield 78%). Recrystallization from methanol gave needles having a melting point of 207–208° C.

The methyl ester obtained (74.4 mg) was treated with ethanolic sodium hydroxide (2N) and the mixture was then neutralized. The theoretical amount of 5-(5,6,7,8-tetrahydro5,5,8,8-tetramethyl-2-naphthalenylcarbamoyl)pyridine-2-carboxylic acid was obtained. Recrystallization from ethyl acetate and n-hexane gave prisms having a melting point of 200—201° C. (69.5 mg, yield 97%).

Elemental Analysis ($C_{21}$ $H_{24}N_2O_3H_2O$) Calc. C: 68.09%; H: 7.07%; N: 7.56% Found C: 68.07%; H: 7.12%; N: 7.47%

Example 2:

6- ( 5,6,7,8-Tetrahydro-5,5,8,8-tetramethyl-2naphthalenylcarbamoyl) pyridine-3 -carboxylic acid By using pyridine-2,5-dicarboxylic acid 5- monomethyl ester, methyl 6-( 5,6,7,8-tetrahydro-5,5,8,8-tetramethyl- 2-naphthalenylcarbamoyl)pyridine-3-carboxylate was obtained as needles in the same manner as Example 1 (melting point 176°-177° C., yield 36%).

The methyl ester obtained above was treated with ethanolic sodium hydroxide (2N) and the mixture was then neutralized. 6-(5,6,7,8-Tetrahydro-5,5,8,8-tetramethyl-2-naphthalenylcarbamoyl) pyridine-3-carboxylic acid was obtained in a yield of 83%. Recrystallization from ethyl acetate and n-hexane gave needles having a melting point of 205.5–207° C.

Elemental Analysis ($C_{21}H_{24}N_2O_3$) Calc. C: 71.57%; H: 6.86%; N: 7.95% Found C: 71.50%; H: 6.70%; N: 7.69%

Example 3

3-Hydroxy-4-(5,6,7,8-tetrahydro-5,5,8,8-tetramethyl-2-naphthalenylcarbamoyl)benzoic acid The starting material, 2-hydroxy-terephthalic acid 4monomethyl ester, was obtained by preparing 2-hydroxy-terephthalica acid from the diazonium salt of 2-amino-terephthalic acid dimethyl ester, and successively monomethylating the result using methanolsulfric acid. The resulting 4-carboxylic acid methyl ester (417 mg) Was dissolved in 30 ml of ethyl acetate and 4-dimethylaminopyridine (51 mg) was added. To the solution, a solution of dicyclohexylcarbodiimido (442 mg, 1 eq.) in ethyl acetate (10 ml) was added, and then a solution of 5,6,7,8-tetrahydro-5,5,8,8-tetramethyl-2-naphthylamine (454 mg) in ethyl acetate was added. After being allowed to stand overnight, the reaction mixture was extracted with ethyl acetate after water was added to the mixture. The extract was washed with 2N HCl, water, and 1N NaHCO3 and dried, and then concentrated to remove the solvent. The residue was chromatographically purified using a small amount of silica-gel to give methyl 3-hydroxy-4-(5,6,7,8-tetrahydro-5,5,8,8-tetramethyl-2-naphthalenylcarbamoyl)benzoate (281 mg, yield 35%). The needles obtained by recrystallization from methylene chloride and n-hexane had a melting point at 200 ° C.

The methyl ester obtained (64.0 mg) was treated with ethanolic sodium hydroxide (2N) and the mixture was then neutralized. 3-Hydroxy-4-(5,6,7,8-tetrahydro-5,5,8,8-tetramethyl-2naphthalenylcarbamoyl)benzoic acid was obtained (52.5 mg, yield 85%). Recrystallization from methylene chloride and methanol gave needles having a melting point of 286°-287° C.

Elemental Analysis ($C_{22}H_{25}NO_4$) Calc. C: 71.91%; H: 6.85%; N: 3.81% Found C: 71.62%; H: 6.88%; N: 3.71%

Example 4

3-Hydroxy-4-(5,6,7,8-tetrahydro-5,5,8,8-tetramethyl-2-naphthalenylcarboxamide)benzoic acid 5,6,7,8-Tetrahydro-5,5,8,8-tetramethyl-2-naphthalecarboxylic acid (998 mg) was treated with an excess amount of thionyl chloride to afford acid chloride. The acid chloride was then dissolved in dry benzene (30 ml) and the solution was refluxed for 1 hour after methyl 4-amino-3-oxybenzoate (647 mg) was added. After water was added, the reaction mixture was extracted to give methyl 3-hydroxy-4-(5,6,7,8-tetrahydro-5,5,8,8-tetramethyl-2-naphthalenylcarboxamide)benzoate having a melting point of 249°-251° C. (589mg, yield 38%).

Hydrolyzation of the ester obtained (120 mg) using 2N-NaOH gave the theoretical amount of 3-hydroxy-4-(5,6,7,8-tetrahydro-5,5,8,8-tetramethyl-2-naphthalenylcarboxamide)benzoic acid (recrystallized from methanol; m.p. not less then 300° C.).

Elemental Analysis ($C_{22}H_{25}NO_4$) Calc. C: 71.91%; H: 6.85%; N: 3.81% Found C: 71.68%; H: 6.80%; N: 3.72%

Example 5

6-(3,4-Di-isopropylphenylcarbamoyl)pyridine-3-carboxylic acid

Pyridine-2,5-dicarboxylic acid 5-methyl 71 ester (120 mg) was dissolved in 20 ml of dry benzene, and the solution was refluxed for 5 hours after 2.0 ml of thionyl chloride was added. The solvent and excess thionyl chloride was removed by evaporation under a reduced pressure, and then trace thionyl chloride in the residue was removed by two azeotropic distillations under a reduced pressure using 2 ml of benzene. The residue was dissolved in 10 ml of dry benzene, and 117 mg of 3,4-diisopropylaniline in the mixture of 0.5 ml of dry pyridine and 10 ml of dry benzene was added to the solution with stirring and a further stirring was continued for 30 minutes under argon atmosphere at 22° C. The reaction mixture was poured into 50 ml of ice-water, and the mixture was vigorously mixed with 2 ml of 2N hydrochloric acid. The mixture was extracted with ethyl acetate, dried over anhydrous sodium sulfate, and the solvent was then removed to give 231 mg of yellow-brown crude solid. The resulting solid was chromatographically purified using silica gel to give 201 mg of pale yellow solid. Recrystallization from n-hexane and ethyl acetate gave methyl 6-(3,4-Di-isopropylphenylcarbamoyl) pyridine-3-carboxylate as pale yellow prisms having a melting point of 160°-161° C. (147 mg, yield 65.4%).

Elemental Analysis ($C_{20}H_{24}N_2O_3$) Calc. C: 70.57%; H: 7.11%; N: 8.36% Found C: 70.28%; H: 7.11%; N: 8.53%

The methyl ester obtained above (120 mg) was dissolved in 20 ml of methanol and the solution was stirred at 21° C. for 12 hours after 4 ml of 2N NaOH was added. After neutralization and extraction, 6-(3,4-Di-isopropylphenylcarbamoyl)pyridine-3carboxylic acid was obtained (92 mg). Recrystallization from n-hexane and ethylacetate gave pale yellow prisms having a melting point of 188-189.5 ° C.

Elemental Analysis ($C_{19}H_{22}N_2O_3$) Calc. C: 69.92%; H: 6.79%; N: 8.58% Found C: 69.72%; H: 6.92%; N: 8.33%

Example 6

5-(3,4-Di-isopropylphenylcarbamoyl)pyridine-2-carboxylic acid

Pyridine-2,5-dicarboxylic acid 2-methyl ester (281 mg) was dissolved in 30 ml of dry benzene, and the solution was refluxed for 3 hours after 2.0 ml of thionyl chloride was added. The solvent and excess thionyl chloride was removed by evaporation under a reduced pressure, and then trace thionyl chloride in the residue was removed by two azeotropic distillations under a reduced pressure using 2 ml of benzene. The residue was dissolved in 10 ml of dry benzene, and 238 mg of 3,4-diisopropylaniline in the mixture of 0.5 ml of dry pyridine and 10 ml of dry benzene was added to the solution with stirring and a further stirring was continued for 10 minutes under argon atmosphere at 25° C. The reaction mixture was poured into 50 ml of ice-water, and the mixture was vigorously mixed with 2 ml of 2N hydrochloric acid. The mixture was extracted with ethyl acetate, dried over anhydrous sodium sulfate, and then the solvent was removed to give 426 mg of yellow-brown oil. The resulting oil was chromatographically purified using silica gel to give 392 mg of pale yellow solid. Recrystallization from n-hexane and ethyl acetate gave methyl 5-(3,4-Di-isopropylphenyl-carbamoyl) pyridine-2-carboxylate as pale yellow prisms having a melting point of 122°–123.5° C. (348 mg, yield 73.5%).

Elemental Analysis ($C_{20}H_{24}N_2O_3$) Calc. C: 70.57%; H: 7.11%; N: 8.36% Found C: 70.45%; H: 7.16%; N: 8.29%

The methyl ester obtained (102 mg) was dissolved in 20 ml of methanol and the solution was stirred at 24° C. for 8 hours after 4 ml of 2N NaOH was added. After neutralization and extraction, 5(3,4-Di-isopropyl-phenylcarbamoyl)pyridine-2-carboxylic acid was obtained (81 mg). Recrystallization from n-hexane and ethylacetate gave pale yellow prisms having a melting point of 199–199.5° C. (68 mg, yield 72.6%).

Elemental Analysis ($C_{19}H_{22}N_2O_3$) Calc. C: 69.92%; H: 6.79%; N: 8.58% Found C: 70.00%; H: 6.71%; N: 8.49%

EXPERIMENT

The activities of the compounds of the above-described examples on differentiation were evaluated using promyelocytic leukemia cell-line HL-60 according to the method described in Japanese Patent Unexamined Publication No. 61-76440. The differentiation to granulocyte was evaluated by morphological observation of nucleus and measurement of ability to reduce nitroblue-tetrazolium (NBT). These are well known procedures providing adequate results in the evaluation of the cell differentiation-inducing activity of retinoids. Retinoic acid was used as the reference compound, and the concentrations which induced differentiation in the half of the cells were calculated. The results are summarized in Table 1.

TABLE 1

| Differentiation Inducing Activity on HL-60 | |
|---|---|
| Compound tested | $ED_{50}$ (M) |
| Retinoic Acid | $2.4 \times 10^{-9}$ |
| Compound of Example 1 | $4.0 \times 10^{-8}$ |
| Compound of Example 2 | $2.2 \times 10^{-10}$ |
| Compound of Example 3 | $4.1 \times 10^{-10}$ |
| Compound of Example 4 | $6.5 \times 10^{-9}$ |
| Compound of Example 5 | $2.5 \times 10^{-8}$ M |

What is claimed is:

1. A carboxylic acid compound represented by the following formula:

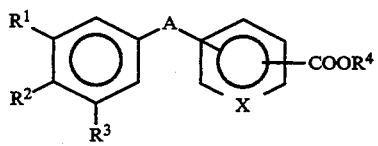

wherein $R^1$, $R^2$, and $R^3$ independently represent a hydrogen atom or an alkyl group of at least two carbon atoms wherein at least two of $R^1$, $R^2$, and $R^3$ represent an alkyl group of at least two carbon atoms; $R^4$ represents a hydrogen atom or an alkyl group; A represents —CO—NH— or —NH—CO—; and wherein A is in a para position relative to $COOR^4$.

2. A pharmaceutical composition comprising an effective amount of a carboxylic acid compound represented by the following formula:

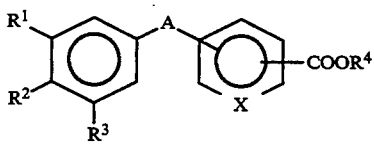

wherein $R^1$, $R^2$, and $R^3$ independently represent a hydrogen atom or an alkyl group of at least two carbon atoms wherein at least two of R, $R^2$, and $R^3$ represent an alkyl group of at least two carbon atoms; $R^4$ represents a hydrogen atom or an alkyl group; A represents —CO—NH— or —NH—CO—; and wherein A is in a para position relative to $COOR^4$; together with a pharmaceutically acceptable carrier or coating.

3. 6-(3,4-Di-isopropylphenylcarbamoyl)pyridine-3-carboxylic acid.

4. 5-(3,4-Di-isopropylphenylcarbamoyl)pyridine-2-carboxylic acid.

* * * * *